United States Patent [19]

Hoots et al.

[11] Patent Number: 5,006,311
[45] Date of Patent: Apr. 9, 1991

[54] MONITORING PERFORMANCE OF A TREATING AGENT ADDED TO A BODY OF WATER

[75] Inventors: John E. Hoots, St. Charles; Rodney H. Banks, Naperville, both of Ill.

[73] Assignee: Nalco Chemical Company, Naperville, Ill.

[21] Appl. No.: 497,681

[22] Filed: Mar. 23, 1990

[51] Int. Cl.$^5$ .................... G01N 21/00; G01N 31/00; G01N 33/00
[52] U.S. Cl. ............................ 422/62; 422/3; 436/56; 210/745
[58] Field of Search .................... 436/73, 2, 56; 422/3, 422/62; 210/745, 759, 696

[56] References Cited

U.S. PATENT DOCUMENTS

| | | | |
|---|---|---|---|
| 3,605,775 | 12/1971 | Zaander et al. | 210/745 |
| 4,217,544 | 12/1980 | Schmidt | 436/6 |
| 4,478,941 | 10/1984 | Hillshafer | 436/56 |
| 4,659,676 | 4/1987 | Rhyne, Jr. | 436/56 |
| 4,783,314 | 11/1988 | Hoots et al. | 422/62 |
| 4,820,647 | 4/1989 | Gibbons | 436/73 |

FOREIGN PATENT DOCUMENTS 0320086  6/1989  United Kingdom ................ 210/745

Primary Examiner—Robert J. Warden
Assistant Examiner—Laura E. Collins
Attorney, Agent, or Firm—Kinzer, Plyer, Dorn, McEachran & Jambor

[57] ABSTRACT

Analyzing the level of a treating agent and/or stress metals in a body of water containing an inert transition metal tracer added to the water proportionally with the treating agent by determining the absorbance (first absorbance value) of a reagent dye added to water, said dye producing a second absorbance value when reacted at the same concentration with the tracer and stress metals in a measure of said body of water, and said dye producing a third absorbance value when reacted at the same concentration with only the transition metal contained in a measure of said body of water; determining the second and third absorbance values and resolving their differences to determine the concentration of the tracer and, separately, the concentration of said stress metals.

8 Claims, 2 Drawing Sheets

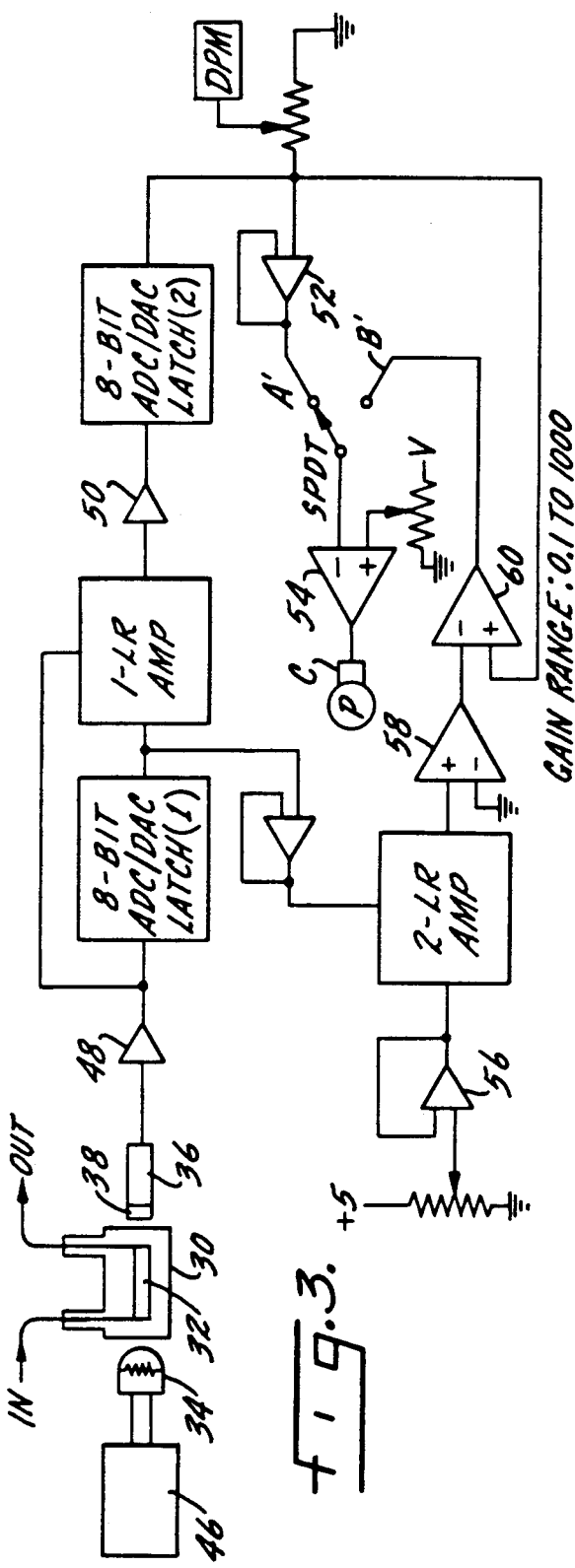
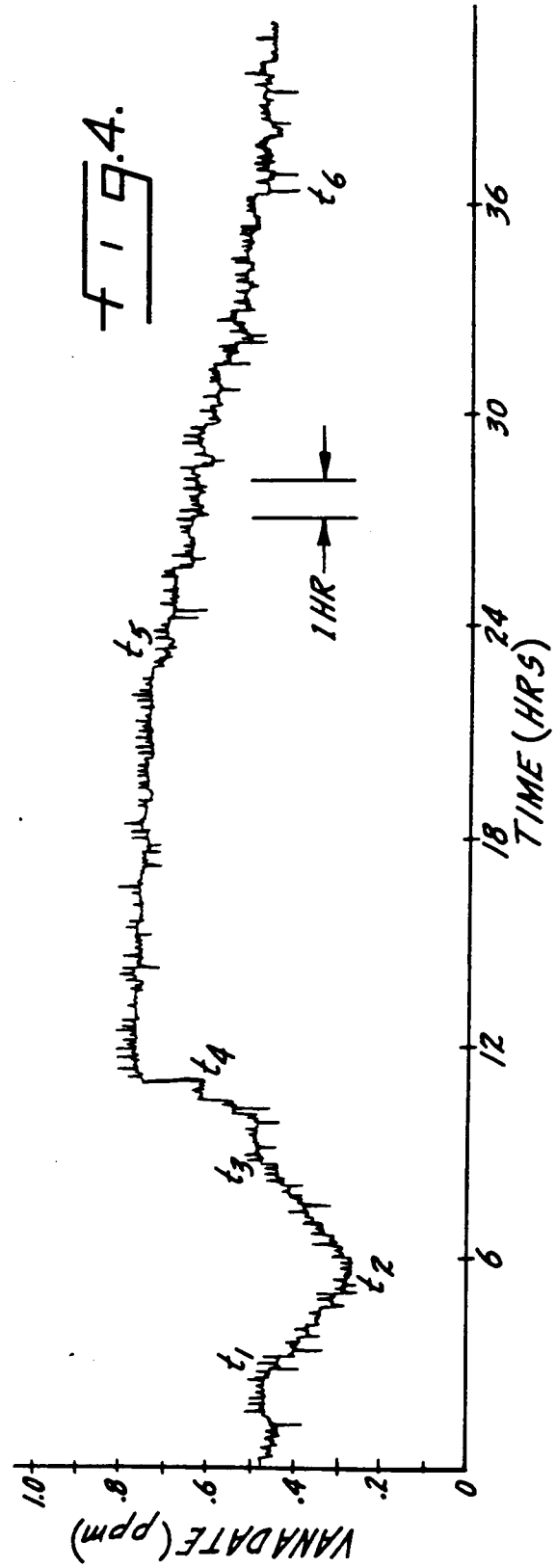

MONITORING PERFORMANCE OF A TREATING AGENT ADDED TO A BODY OF WATER

FIELD OF THE INVENTION

This invention relates to on-stream monitoring of the level of a treating agent added to a moving body of water. The treating agent is added to improve the quality of the water such as by reducing the scaling tendency, hardness, corrosion influence, suspended solids, and so on.

The typical water system is a water cooling tower where water is used in a heat exchange role. Because the expensive equipment may be exposed to impure water, and because the heat exchange surfaces need to be clean, the water is treated with an anti-corrosion, anti-scaling agent. To optimize use of the treating agents, it is therefore advantageous to determine if the consumption of treating agent is in accordance with recommended use levels specific to the environment. If there is an undertreatment, deposition of scaling salts and corrosion may rapidly occur; if there is an overtreatment, chemicals will be wasted.

A non-consumable or system-inert tracer can be proportioned to the treating agent in terms of initial concentration added to the system. This is the "standard". If the treating agent is added at a rate equal to or greater than the recommended rate, as it should be, the concentration of tracer:treating agent will increase proportionally. This increase, monitored, can be compared to the recommended or theoretical standard to determine if there is indeed par performance, that is, whether the sample: standard color intensity comparison shows the treating agent is present at the expected concentration. If not, there are several predominant possibilities: there is an undertreatment to the detriment of the equipment, there is an overtreatment which is a waste, or water in the system is being unexpectedly lost along with the treatment chemical. The first two possibilities involve a correction in the dosage of treating agent. The third possibility calls for a system audit which in a water cooling tower system would amount to a check as to whether there is an unexpected source of "blowdown" water which removes substances from the system, an unexpected source of "make-up" water, and so on. Blowdown is periodically undertaken to remove water with a high concentration of impurities; make-up water of higher purity is added to maintain the system balance, due to evaporation, for example. Thus, the tracer concentration can be taken as a measure of chemical treatment and can provide an indication of when parts of the system are not operating properly.

These factors in a water cooling tower system can be better visualized by considering a few generic equations.

The term concentration ratio (CR) is a measure of changes in the level of dissolved or suspended matter, $$CR = \frac{\text{concentration of cooling water salts}}{\text{concentration of make-up water salts}}$$

To maintain a proper CR, blowdown removal (B) and make-up additives (M) are adjusted, especially as may be needed because of evaporation, (E). The factors are interrelated and vary due to weather, water quality, operating rates and so on. Thus, $$E = B + M$$

and $$CR = M/B$$

Blowdown can occur in a variety of (sometimes unknown or unreported) ways, and is seldom predictable or is not well defined because of the enormity of cooling water systems. Evaporation rate may undergo a sudden change.

Consequently, the feed rate (dosage) of chemical treatment is commonly an estimate (theoretical) which in turn depends upon several complex and variable factors. Under changing operating conditions, the dosage will also change, and hence the need for accurate, precise monitoring of the tracer. The system may respond at different rates to the dosage change, until equilibrium is reached.

The tracer must be unreactive in the system water for predictable results. The present invention is concerned with a unique tracer and analytical instrumentation mated to the nature of the tracer.

Systems other than cooling tower recirculating water can be similarly postulated: boiler water flow, where water hardness is of particular concern; clarification flow, where settling solids is of particular concern, and so on, wherever there is a moving body of industrial or municipal water requiring dosage with a treating agent to enhance water quality.

U.S. Pat. No. 4,783,314 (John Hoots) presents a thoroughgoing analysis of the use of a fluorescent tracer to monitor treating agent performance in such water systems; pending application Ser. No. 258,131, filed Oct. 14, 1988, discloses instrumentation by which monitoring can be conducted continuously. Those disclosures elaborate background information which need not be repeated here.

We also acknowledge the disclosure in our co-pending application Ser. No. 315,713, filed Feb. 27, 1989, in which there is a disclosure of the vanadate transition metal tracer which features in the preferred embodiment of the present invention.

SUMMARY OF THE INVENTION

Many tracers heretofore employed are now deemed environmentally objectionable, can be difficult to distinguish from stress metals (e.g. iron ions which affects treatment performance) and not susceptible to accurate analysis at low concentrations. A low concentration is desirable in order to assure the tracer is widely dispersed, effectively isolated from disturbances, as compared to high concentrations where the chances of losing linear detector response versus trace level are increased.

One object of the present invention is to circumvent these limitations by employing a tracer, selected from the class of transition metals, to determine treating agent performance, and which, at the same time, permits us to determine quantitatively other uncompensated chemical stresses, such as contamination by iron ions, both measurements achieved by reagents which in effect allow an absorbance (color intensity) subtraction mode of measurement by an absorbance sensor.

We achieve this objective in part by a combination of a transition metal tracer, preferably vanadate, and a complementary dye. The dye reacts with stress metals present in the water (iron for example) and reacts with the transition metal tracer at the same time to produce a "sample" with a distinct color or color intensity having an absorbance value (II); by rendering the transition metal tracer unreactive (vanadate for example), in a specimen termed the "blank", a different color or color intensity is obtained with an absorbance value, I. By subtracting (II−I) the prevailing concentration of the transition metal tracer is obtained which is equated to the concentration of the treating agent present in the system. Thus, "sample" minus "blank" equals tracer value.

Then, by measuring the absorbance of the dye in distilled water (III), it is possible by a second subtraction (I−III) to determine the level of stress metals, if any is present. Additional measures of operating system stresses can be supplied by one or more other sensors (e.g. temperature, pH, conductivity, calcium, suspended solids and so on) and the results used to modify the result of the sensor employed with the transition metal indicated for stress metals. The final combined result can be used to indicate treatment level relative to actual needs of a cooling water system.

Consequently, it becomes possible to monitor the treating agent level for par performance (adjusting the dosage if needed) and, separately, to then identify any prevailing chemical or operating condition stress while adjusting the product dosage accordingly.

The stress metals (contamination) to which we refer may include iron, nickel, copper and zinc. This stress, when present, regardless of quality, may call for an increase in the dosage of treating agent, or that the treating agent level be modified to compensate for changes in the operating conditions.

In our co-pending application we disclose the use of transition metals, including vanadate, as tracers to check treating agent levels; in this instance we go a step further by monitoring chemical and operating condition stresses, and we also develop instrumentation by which that step may be accomplished. Other transition metals may be used as tracers based on choice of selective analysis method or additionally, blanking procedure which distinguishes tracer level from chemical and operating condition stresses. However, vanadate is preferred because the reagent to neutralize it ($H_2O_2$) is inexpensive and easy to handle. The reagent reacts with the vanadate tracer (V) to produce an ionic form that is unreactive with the dye. The vanadate tracer may be derived from various compounds, typically vanadate salts of sodium, potassium and ammonium.

BRIEF DESCRIPTION OF THE DRAWING

FIG. 3 is a diagram of the circuitry for resolving and using voltage values; and FIG. 4 replicates a performance chart recording.

DETAILED DESCRIPTION

1. Treating Agent Concentration

The dye we prefer to employ for colorimetry is pyridyl azo resorcinol, PAR. It will react with a vanadate to produce a color complex (V-PAR) having a particular absorbance value when illuminated at a particular wavelength. This dye will also react with stress metal ions (e.g. Fe) to produce a color complex FePAR having a different color or color intensity, and therefore different absorbance. The vanadate ion in the system water may be added as $VO_4(^{-3})$ or $VO_3(^{-1})$.

Figure 1:
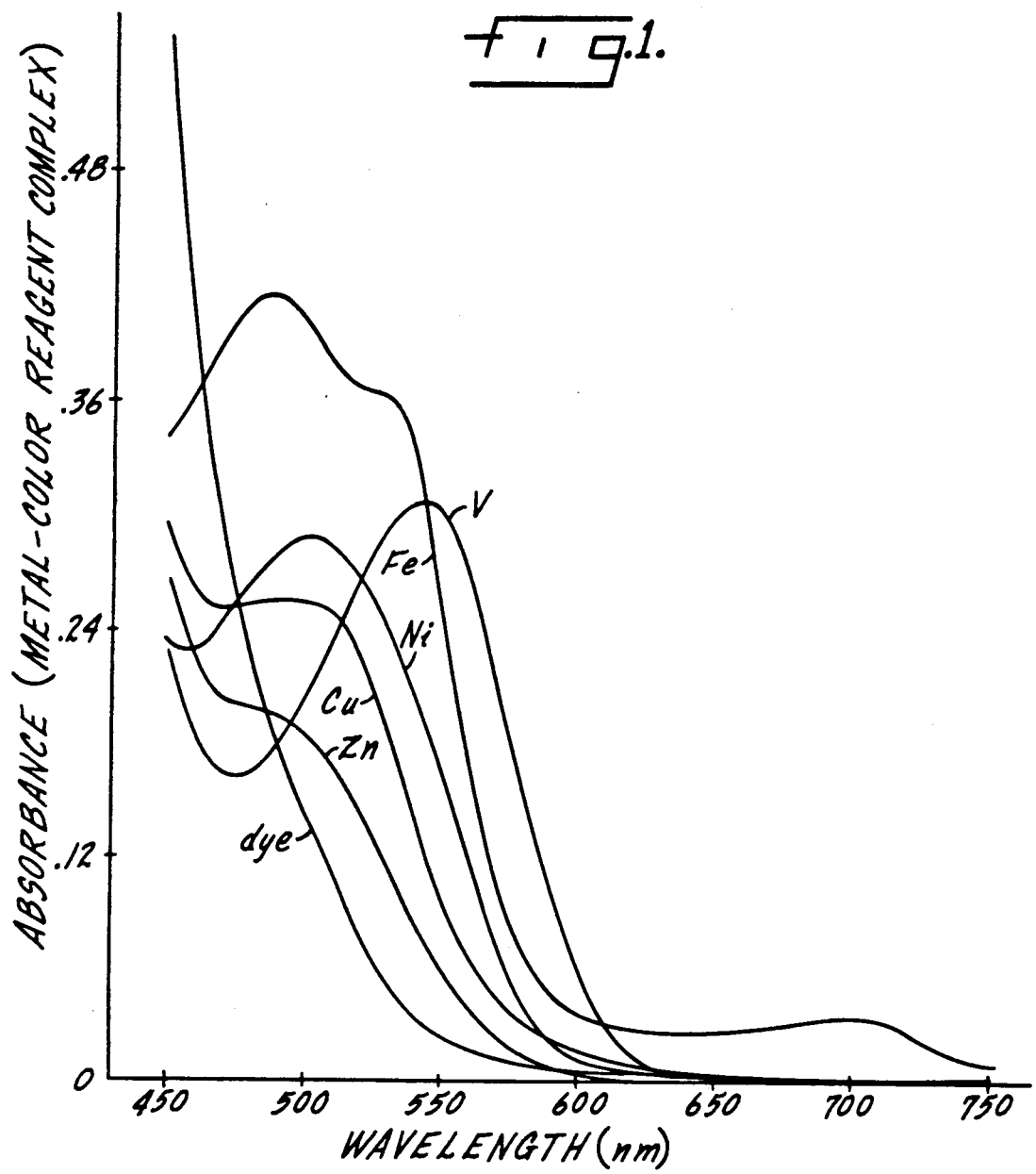
FIG. 1 presents curves showing changes in absorbance values for metal-color reagent complexes for different metals (all at 0.5 ppm) at different wavelengths of light.

Referring to FIG. 1 (all metals at 0.5 ppm in distilled water), these curves exhibit absorbance vs. wavelength for the dye and for its reaction product with vanadate (V) and the stress metals. There is considerable interference at about 545 nm, but by operating the instrumentation hereinafter disclosed at about 570 nm, there is sufficient sensitivity to minimize interference of V-PA with the other dye-metal complexes. These other metal complexes derived from the stress metals will be abbreviated as M-PAR collectively.

While masking agents such as EDTA and NTA will prevent the interference, these masks inhibit the necessary V-PAR reaction. A satisfactory solution to this problem, leading up to our ability to measure the stress metal content, is to selectively inhibit the transition metal reaction, V-PAR in a "Blank" and then subtract the absorbance of the Blank from an uninhibited Sample in which the absorbances of both V-PAR and M-PAR are present:

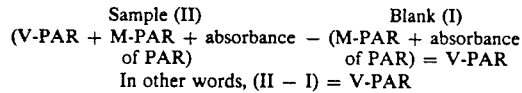

Sample (II)       Blank (I)
(V-PAR + M-PAR + absorbance − (M-PAR + absorbance
         of PAR)                 of PAR) = V-PAR
In other words, (II − I) = V-PAR Inhibition is achieved by withdrawing a portion of the system water containing the vanadate tracer and treating it with $H_2O_2$ at about pH 5 where the vanadate value at equilibrium becomes $VO_2^+$ in the Blank:

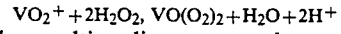

$VO_2^+ + 2H_2O_2, VO(O_2)_2 + H_2O + 2H^+$

The resulting diperoxyvanadate anion does not react with PAR to form a color complex. The Blank is passed through the instrument to measure absorbance (I).

A second portion withdrawn from the system water (the Sample) is not reacted with peroxide and hence its absorbance is biased by the absorbance value of V-PAR. The Sample is passed through the instrument to measure absorbance (II).

The absorbance values are converted to a voltage analog which may be digitized so that there can be a digital readout equivalent to the concentration of the vanadate tracer, that is, the equivalent of the concentration of the treating agent. The instrumentation is calibrated so that the prevailing treating agent concentration may be compared to the theoretical range. The range limits may be denoted by high and low set points at a comparator preceding the controller for the pump. If the voltage is outside the set points a signal will be generated by the comparator to start or stop the pump which adds the treating agent dosage.

2. Chemical Stress

Though the treatment concentration may very well be within the set or theoretical range, not requiring any change in dosage administered by the pump, there may be, even on a hourly basis, unexpected stressing by unneutralized ions of iron, nickel, copper, and zinc as noted above. Their measure may be taken by what may be termed a second subtraction, which, in the instrumentation, involves the step of preserving (storing) the absorbance value or voltage equivalent of the Blank and biasing it with the absorbance value of PAR alone. The bias is a second subtraction process.

To obtain the absorbance of the dye, PAR, it (by itself) is added to a portion of distilled water in the same concentration as employed for the on-stream analysis. This may be termed the DI Blank which is passed through the instrument so that the DI Blank absorbance may be measured, III. Hence, $$Blank - DI\ Blank = I - III = Chemical\ Stress$$

While it is possible to employ instrumentation in which the second subtraction stands by itself to be used as a correction value, we prefer to store the absorbance value of (I) and ratio or bias it by III, by the mere flip of a switch, so to speak, once the absorbance value of PAR has been determined and transformed to its voltage equivalent.

3. Analytical Procedure and Instrumentation

The tracer will have been added to the system water (e.g. tower water) in a proportioned amount with the treating agent. The amount of tracer (vanadate) in the treating agent is typically 0.5% by weight, or 0.5 ppm in the tower at a treating agent level of 100 ppm.

Figure 2:
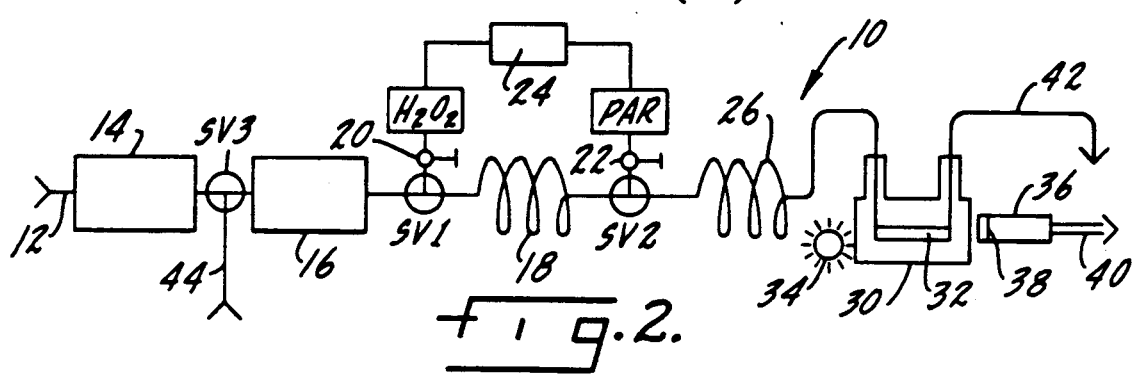
FIG. 2 is a diagram of the analytical instrumentation and operating procedure.

The system sample to be monitored is passed through an on-line analyzer 10, FIG. 2, which performs an analysis automatically, displays the vanadate concentration in ppm, produces a corresponding control voltage to the pump which supplies the treating agent if its concentration is out of the rang and imposes a further control on the pump if metal stressing is detected.

The analyzer 10 has an inlet 12 to a filter 14 for the solution to be analyzed, being drawn into and passed through the analyzer by a microgear pump 16 at the rate of 5 ml/min.

The pathway (plastic tubing) includes two three-way solenoid valves SV1 and SV2 separated by an $H_2O_2$ mixer 18.

The $H_2O_2$ reagent is admitted to valve SV1 by a needle valve 20; the PAR reagent is admitted to valve SV2 by a needle valve 22. Both reagents are under a slight pressure head (3 psi) supplied by an inert gas source 24.

Downstream of valve SV2 is a second mixer 26 where the PAR reagent is mixed. From the mixer 26 the pathway leads to a chamber 30 which includes a flow cell 32 (1 cm pathlength, 80 l volume) illuminated by a tungsten-halogen lamp 34.

The liquid being analyzed flows through cell 32 of course. The cell is made of quartz, transparent to visible light emitted by lamp 34 and the absorbance of the liquid in cell 32 is registered by a detector 36 having a 570 nm light filter 38. The absorbance value 40 is transmitted to the instrumentation analog circuitry, FIG. 3, and the liquid flowing out of cell 32 is returned to waste at 42.

The preferred arrangement for determining absorbance is that of FIG. 2, but other arrangements may be employed. The reagents may be syringe-pumped, gravity-fed, or introduced under pressure. The liquid entrance 12 and its forced flow to the cell 32 may likewise be altered.

The solenoid valves are programmed automatically to open and close to admit the required reagent once the main control switch of the analyzer is closed, and of course the solenoid valves are synchronized thereto and to one another so that known amounts of $H_2O_2$ and PAR are added to the system water as required for analysis of the Blank (I), the Sample (II) and the DI Blank (III). Also, the timing is such that the flow cell holds a static load for sufficient time (about 60 sec.) to enable the absorbance reading to reach the steady state, true value.

3a. Absorbance of the Blank ($I_A$)

When analyzing the Blank (I) both reagents are employed. The $H_2O_2$ reagent (contained at $H_2O_2$, FIG. 2) is a commercial grade (3% $H_2O_2$) to be added through the needle valve 20 in the volumetric ratio of 1:80, that is, one volume of 3% $H_2O_2$ to 80 volumes of the on-stream system water. As noted this reagent prevents a color reaction between the dye and the vanadate.

The PAR dye reagent, contained at PAR, FIG. 2, is in solution (wt %) as follows:

| | |
|---|---|
| 50.5 | methanol |
| 42.0 | water (distilled) |
| 7.0 | succinic acid half neutralized with NaOH |
| 0.01 | PAR |
| 0.5 | 1,2-diacetylhydrazine (DAH) |

Methanol serves as a co-solvent with water to increase the stability of PAR. The neutralized succinic acid buffers the pH at about 5 to 5.5. The DAH is a safety to assure any chlorine (biocide) is scavenged to protect the PAR from oxidation. This reagent is allowed a reaction time of about one minute after addition of $H_2O_2$ to assure full color development, characteristic of any chemical stress metals present since V-PAR is excluded by $H_2O_2$.

The PAR reagent solution is added in the volumetric ratio (v/v) of 5 parts of on-stream tower water to 1 of PAR reagent. After the time lapse noted, the absorbance of the Blank is taken ($I_A$) and transmitted to the signal processing circuitry, FIG. 3.

3b. Absorbance of the Sample ($II_A$)

The analytical process is the same as explained under heading 3above, except the hydrogen peroxide, which reacts with the vanadate, is not used, only the PAR reagent; hence the absorbance reading is a sum of all metal ions, including vanadium in the Sample. The Sample absorbance value ($II_A$) is converted to a voltage analog in the process circuitry, FIG. 3, where it is ratioed or otherwise resolved with the absorbance value $I_B$ of the Blank; an output voltage then becomes proportional to the vanadate tracer concentration.

3c. The Absorbance of the DI Blank ($III_A$)

The specimen to be measured for absorbance will be distilled water (DI) injected only with the PAR reagent. No system water is present. The distilled water may be admitted via inlet 44, FIG. 2, upon appropriately setting a third 3-way solenoid valve SV3. The volumetric proportions are the same, DI:PAR being 5:1. The absorbance reading will be that for PAR only, $III_A$ or PARA. In reality, the absorbance value is a constant, enabling the absorbance of the chemical stress to be quantified, or at least considered empirically, namely, $$I_A - III_A = Chemical\ Stress$$

Since the voltage equivalent of $PAR_A$ is a constant, it may be used as a correcting bias as hereinafter explained.

It may be noted incidentally that subtraction of absorbance values have been used as the best simplification for understanding the meaning of the successions of absorbance readings.

3d. Instrumentation Circuitry

The instrumentation for deriving voltage equivalents of the absorbance values is shown in FIG. 3 where a portion of FIG. 2 is repeated. The lamp 34 is a tungsten-halogen lamp focused on the flow cell 32; the power source for the lamp is identified at 46. The detector 36 and its filter 38 transform the absorbance to voltage passed through a voltage follower 48.

The voltage of the Blank ($V_1$) is delivered to an 8-bit ADC/DAC Latch (1) and stored there until needed.

The voltage value of the Sample ($V_2$) is shunted around the latch and is received by a log ratio amplifier 1-LR AMP where it is ratioed with the voltage value of the Blank released from storage in the cycle in which the ratio is to be made. Thus, the significant voltage output of 1-LR AMP is proportional to $$\log \frac{\text{Blank voltage}}{\text{Sample voltage}} = \log V_1/V_2$$

transmitted to a second 8-bit storage latch ADC/DAC Latch (2) via a voltage follower 50. The output voltage (the log ratio voltage Blank:Sample) is transformed to a digital readout displayed at a monitoring panel DPM and is also sent through a voltage follower 52 producing voltage output A' which is delivered to a comparator 54 where signal A' is compared to the standard or theoretical voltage representing par performance. If performance is non-par, the comparator passes a voltage signal to the controller C of the pump P which doses the system with the proportioned amount of treating agent:-tracer. Voltage output A' may be abbreviated A' (proportional to)[Abs V]

standing for a signal to the comparator proportioned to the vanadate absorbance reading, equivalent to the concentration of the treating agent to be compared to the standard.

Chemical stress is the next check on system performance. The DI BLANK absorbance, as noted above, will be a constant. Its voltage equivalent ($V_3$) may therefore be delivered to a voltage follower 56 and transmitted to a second log ratio amplifier 2-LR AMP which also receives the stored value of the BLANK from Latch (1) as will be apparent in FIG. 3, emitting a voltage signal proportional to $$\log \frac{DI \text{ Blank voltage}}{\text{Blank voltage}} = \log V_3/V_1$$

which is amplified at 58 and at 60 is combined with the output from Latch (2) resulting in pump signal B', correcting for chemical stress, if detected. This signal B' may be abbreviated as proportional to

[Abs V]−[Abs (Blank−DI Blank)]

It is not necessary to an understanding of this disclosure to diagram the timing circuitry by which the solenoid valves and pump (FIG. 2) are sequenced by relays, nor the timing circuitry by which the latched information is released from storage in timed sequence to the log ratio amplifiers, FIG. 3. That is a matter of computer programming.

In summary, determination of the vanadate concentration (absorbance of the sample minus absorbance of the blank) tells if the treating agent is being consumed within the range deemed theoretically sufficient to improve the quality of the system water by neutralizing the impurities.

No stress metal correction

Take 100 ppm as theoretical optimum detected rate for the treating agent at equilibrium. If the measured level drops below 100, say 70 ppm, for example, then an increase in treating agent feedrate is required. If the measured value rises above 100, say 130, then there exists an overdosing condition and feedrate should be reduced. This is given by output A'.

Stress metal correction

In addition to the above, if the equilibrium concentration is set at 100 ppm but there is an increase in system stress metals, then the measured tracer level will drop to, say, 90 ppm, calling for an increase in treating agent feedrate. This is given by B'. By a flip of the SPDT switch in FIG. 3, either mode can be selected.

These empirical situations can be better visualized from FIG. 4 which is an actual print-out of the performance of the vanadate tracer, deemed to exhibit normal performance of the treating agent at about 0.4 to 0.5 ppm. At the beginning, after the pump was turned on, the system equilibrated ($t_1$) at about 0.45 ppm. Afterwards the pump was turned off, whereupon the vanadate gradually declined in concentration to about 0.25 ppm at $t_2$. The pump was restarted to re-establish the norm or par value, $t_3$, enduring about 1 hour. Then, at $t_4$ an overfeed dosage was simulated, and the system was purposely overdosed, resulting in a rise in the vanadate concentration to about 0.75 ppm which prevailed for a long stretch of time to $t_5$ where blowdown in the system resulted in a slowly declining tracer concentration. At $t_6$ control of the treatment dosage was re-established.

Thus, monitoring of the level (consumption) of the treating agent may show substantially more or less than the expected rate, or substantial remnant metal stress, either circumstance placing a demand on the pump controller as a result of voltage comparisons.

Corrections For System Performance Changes

The demands on the pump controller can also be explained and expanded in terms of empirical stress equations. The desired product (treating agent) dosage can be represented by the equation, $$dosage = c_1 + k_1 c_2 + k_2 c_3 \ldots$$

where $c_1$ = recommended product concentration (based on tracer) in the absence of any operating stresses;

$c_2 = (I-III)$ additional product concentration based on stress metal level;

$c_3$ = additional product concentration based on other stresses such as temperature, pH and so on; and $k_1, k_2 \ldots$ are weighting factors based on relative importance of stress factor.

These considerations embrace performance sensor inputs from a variety of sources. A performance-compensated value for treatment dosage is produced, and the vanadate tracer monitor/controller is then used to maintain the corresponding optional dosage.

Hence, while the preferred embodiment of the invention is disclosed and claimed, it is to be understood that variations and modifications may be adopted for equivalent performance by those skilled in the art.

We claim:

1. Method of analyzing the concentration of a treating agent injected by a pump into a body of system water in an amount estimated as optimum for improving the quality of the water, the inject agent being deemed sufficient for optimum performance of the treating agent, consumed as it improves the quality of the water, and also analyzing for the concentration of uncompensated metals constituting chemical stress, which body of water is also injected with an inconsumable vanadate transition metal tracer proportioned to the treating agent concentration as the equivalent of the treating agent concentration, comprising the steps of:

(1) withdrawing a specimen of the body of water and treating it successively with predetermined proportioned amounts of $H_2O_2$ and a dye reactive with both vanadate and stress metal ions, and then measuring the absorbance of the specimen, the $H_2O_2$ preventing the vanadate from reacting with the dye so that the absorbance value (I) of the specimen represents the concentration of stress metals as a blank for comparison; storing the absorbance value of the blank;

(2) withdrawing a second specimen of the body of water as a sample, adding only the predetermined proportioned amount of dye to the sample, without $H_2O_2$; measuring the absorbance (II) of the sample, resolving the difference between absorbance (I) and absorbance (II) to obtain the absorbance value of the vanadate as a measure of the prevailing concentration of the treating agent, and adjusting either the amount of treating agent or volume of water if the resolved absorbance value establishes non-optimum performance of the treating agent;

(3) comparing the absorbance value (III) of the proportioned amount of dye in distilled water to absorbance value (I) and resolving their difference to obtain the absorbance value of any stress metals present.

2. Method according to claim 1 including the step of increasing the dosage of treating agent in an amount to neutralize stress metals which may be present in the system water.

3. Method according to claim 1 including the steps of:

(4) converting the first of the resolved absorbance values to a voltage analog corresponding to the absorbance value of (II−I); and (5) using said resolved voltage analog as a control for said pump to increase or decrease the dosage of treating agent fed to the body of water.

4. Method according to claim 3 including the step of: (6) converting the second of the resolved absorbance values (I−III) to a voltage analog and using that analog to modify the analog control signal of step (4) to the pump to add treating agent to compensate for stress metals.

5. Method for analyzing the concentration level of a treating agent and stress metals in a body of water containing an inert transition metal tracer pumped into a body of water proportionally with the treating agent in treating the system, comprising the steps of:

determining the absorbance (first absorbance value) of a reagent dye when added to water in a certain concentration, said dye producing a second absorbance value when reacted at the same concentration with the tracer and stress metals in a measure of said body of water, and said dye producing a third absorbance value when reacted at the same concentration, with only the transition metal, contained in a measure of said body of water;

determining the second and third absorbance values in successive measures of the body of water;

resolving the differences in said absorbance values to determine the concentration of the tracer and, separately, the concentration of said stress metals;

and altering the pump rate when the resolved differences indicate stress metals substantially uncompensated or when the resolved differences indicate a deviation in the expected level of the treating agent.

6. Method according to claim 5 involving the steps of using the absorbance values to generate voltage analogs representing the resolved absorbance differences, comparing the voltage analogs to voltage values representing optimum performance in the treating agent level and substantial lack of chemical stress in the water system, and controlling the pump in accordance with said comparisons.

7. Method for analyzing the concentration level of a treating agent in a body of water containing an inert transition metal tracer pumped into a body of water proportionally with the treating agent comprising the steps of:

determining the absorbance (first absorbance value) of a reagent dye when added to the body of water in a certain concentration, said dye producing a second absorbance value when reacted at the same concentration with the transition metal contained in a measure of said body of water;

determining the second absorbance value in a measure of the body of water;

resolving the difference in said absorbance values to determine the concentration of the tracer;

and altering the pump rate or conducting an audit of the system when the resolved difference indicates a deviation from the expected treating agent level.

8. Method according to claim 7 involving the step of using the absorbance values to generate a voltage analog representing the resolved absorbance difference, comparing the voltage analog to a voltage value representing optimum level of the treating agent, and controlling the pump in accordance with said comparison.

* * * * *

UNITED STATES PATENT AND TRADEMARK OFFICE
CERTIFICATE OF CORRECTION

PATENT NO. : 5,006,311

DATED : April, 9, 1991

INVENTOR(S) : John E. Hoots and Rodney H. Banks

It is certified that error appears in the above-identified patent and that said Letters Patent is hereby corrected as shown below:

Column 6, line 60, "PARA" should read --PAR$_A$--.

Signed and Sealed this

Sixth Day of October, 1992

Attest:

DOUGLAS B. COMER

Attesting Officer     Acting Commissioner of Patents and Trademarks